United States Patent
Newmark et al.

(10) Patent No.: US 6,982,099 B2
(45) Date of Patent: Jan. 3, 2006

(54) COMPOSITION AND METHOD FOR SMOKE DETOXIFICATION

(76) Inventors: Thomas Newmark, 22 High St., P.O. Box 1947, Brattleboro, VT (US) 05301; Paul Schulick, 22 High St., P.O. Box 1947, Brattleboro, VT (US) 05301

( * ) Notice: Subject to any disclaimer, the term of this patent is extended or adjusted under 35 U.S.C. 154(b) by 0 days.

(21) Appl. No.: 11/001,131

(22) Filed: Dec. 2, 2004

(65) Prior Publication Data

US 2005/0095304 A1    May 5, 2005

Related U.S. Application Data

(62) Division of application No. 10/058,299, filed on Jan. 30, 2002, now Pat. No. 6,827,951.

(60) Provisional application No. 60/267,428, filed on Feb. 9, 2001.

(51) Int. Cl.
 *A61K 35/68* (2006.01)
 *A61K 9/00* (2006.01)
 *A61K 47/00* (2006.01)

(52) U.S. Cl. ............ 424/756; 424/729; 424/400; 424/439; 424/725

(58) Field of Classification Search ........... 424/756, 424/729, 400, 439, 725
See application file for complete search history.

(56) References Cited

*Primary Examiner*—Christopher R. Tate
*Assistant Examiner*—Randall Winston
(74) *Attorney, Agent, or Firm*—Nath & Associates PLLC; Gary M. Nath; Jerald L. Meyer

(57) ABSTRACT

A method is provided for effecting smoke detoxification in a human by using a composition that is made of effective amounts of supercritical extract and hydroalcoholic extract of turmeric.

13 Claims, No Drawings

COMPOSITION AND METHOD FOR SMOKE DETOXIFICATION

This is a divisional of U.S. patent application Ser. No. 10/058,299, filed Jan. 30, 2002 now U.S. Pat. No. 6,827,951.

This application claims the benefit of U.S. Provisional Application No. 60/267,428, filed Feb. 9, 2001.

FIELD OF THE INVENTION

The present invention relates in general to effecting smoke detoxification. In particular, the present invention relates to a turmeric-containing composition to effect smoke detoxification.

BACKGROUND OF THE INVENTION

Tobacco smoke, derived from tobacco smoldering or active smoker exhalation, is a source of human exposure to mutagens and carcinogens. Studies indicate that a close correlation exists between exposure to tobacco smoke and health hazards such as respiratory and cardiopulmonary diseases and lung cancer, in smokers and non-smokers alike. It is known that both active and passive smokers excrete, in their urine, high amounts of tobacco-derived mutagens. In addition, studies have established a connection between human cancer and well-cooked meat (such as, for example, meat cooked on a grill). (See Burros, M., Tea? Turmeric? The Quest for Safer Barbecue, *The New York Times on the Web*, Jul. 5, 2000 (hereinafter "the Burros article")). At high temperatures, creatine in muscle meats react with amino acids, forming cancer-causing compounds called heterocyclic amines. Marination, however, has been used to reduce these heterocyclic amines. Scientists suspect that antioxidants such as garlic, onions, chives, turmeric, thyme, rosemary and oregano, as well as vitamins C and E, assist in reducing such amines. Marination, however, does not reduce the level of other carcinogens, arising, for example, when fat falls on a fire and causes smoke. (See the Burros article).

Turmeric has been found to be effective in inhibiting the formation and excretion of urinary mutagens in smokers. (See P. Kalpagam, T. C. Raghuram, T. P. Krishna and K. Krishnaswamy; "Effect of Turmeric on Urinary Mutagens in Smokers", *Mutagenesis*, vol. 7, no. 2, pp. 107–109 (1992) (stating that tobacco mutagens may be detoxified by the active principle curcumin)). Turmeric has also been found to be an effective anti-mutagen and may be useful in chemoprevention. Articles discussing turmeric and/or curcumin include: Krishnaswamy, K., and Raghuramulu, N., Bioactive Phytochemicals with Emphasis on Dietary Practices, *Indian J Med Res* 108, November 1998, pp. 167–181; Deshpande, S. S., Ingle, A. D., and Maru, G. B., Inhibitory Effects of Curcumin-Free Aqueous Turmeric Extract on Benzo[alpha]pyrene-Induced Forestomach Papillomas in Mice, *Cancer Letters*, 118 (1997) 79–85; Srimal R. C., Turmeric: A Brief Review of Medicinal Properties, *Fitoterapia*, Vol. LXVIII, No. 6, 1997, pp. 483–493; Arbiser, J. L., Klauber, N., Rohan, R., van Leeuwen, R., Huang, M. T., Fisher, C., Flynn, E., Byers, H. R., Curcumin is an In Vivo Inhibitor of Angiogenesis, *Mol Med* (June 1998), 4(6): 376–83; Plummer, S. M., Holloway, K. A., Manson, M. M., Munks, R. J., Kaptein, A., Farrow, S., and Howells, L., Inhibition of Cyclo-Oxygenase 2 Expression in Colon Cells by the Chemopreventive Agent Curcumin Involves Inhibition of NF-kappaB activation Via the NIK/IKK Signaling Complex, *Oncogene* (Oct. 28, 1999), 18(44):6013–20; Singhal, S. S., Awasthi, S., Pandya, U., Piper, J. T., Saini., M. K., Cheng, J. Z., and Awasthi, Y. C., The Effect of Curcumin on Glutathione-Linked Enzymes in K562 Human Leukemia Cells, *Toxicol Lett*, Sep. 20, 1999, 109(1–2):87–95; Kang, B. Y., Song, Y. J., Kim, K. M., Choe, Y. K., Hwang, S. Y., Kim, T. S., Curcumin Inhibits Th1 Cytokine Profile in CD4+ T Cells By Suppressing Interleukin-12 Production in Macrophages, *Br J Pharmacol*, September 1999, 128(2):380–4.

In addition, turmeric may be used to reduce severely elevated fibrinogen levels. (See Ramirez-Bosca A., Soler A., Carrion-Gutierrez, M. A., Mira D. P., Zapata J. P., Diaz-Alperi J., Bernd A., Almagro E. Q. and Miquel, J., A Hydroalcoholic extract of *Curcuma Longa* Lowers the Apo B/Apo A Ratio Implications for Atherogenesis Prevention, *Mechanisms of Ageing and Development* 114 (2000) 207–210. As such, turmeric appears beneficial to the cardiovascular system of persons exposed to smoke.

Eugenol, a compound present in many spices such as cloves, cardamon, etc., has been reported to exhibit antimutagenicity against tobacco smoke. (See Sukumaran K. and Ramadasan K., Inhibition of Tobacco-Induced Mutagenesis by Eugenol and Plant Extracts, *Mutation Research* 343 (1995) 25–30). Moreover, Eugenol is believed to exhibit anti-peroxidative activity. (See. Krishnaswamy, K., and Raghuramulu, N., Bioactive Phytochemicals with Emphasis on Dietary Practices, *Indian J Med Res* 108, November 1998, pp. 167–181).

Reportedly, green tea has chemopreventive effect against cigarette smoke-induced mutations in humans. (See Lee I. P., Kim Y. H., Kang M. H., Roberts C., Shim J. S., and Roh J. K., Chemopreventive Effect of Green Tea (*Camellia sinensis*) Against Cigarette Smoke-Induced Mutations (SCE) in Humans, Journal of Cellular Biochemistry Supplement 27:68–75 (1997)). See, for example, Klaunig J. E., Xu Y., Han C., Kamendulis L. M., Chen J., Heiser C., Gordon M. S., and Mohler III E. R., The Effect of Tea Consumption on Oxidative Stress in Smokers and Nonsmokers, *Antioxidant Effects of Tea*, pp. 249–254 for a discussion of the effect of green tea consumption on oxidative damage induced by cigarette smoking. See, for example, Renqing Z., Zhou Y., Chen D., Shenben L., and Haug A., Effects of Soaking Temperature and Soaking Time During Preparation of Water Extract of Tea on Anticlastogenicity Against Environmental Tobacco Smoke in the Sister-Chromatid Exchange Assay, *Toxicology Letters* 115 (2000) 23–32 for a discussion of the anticlastogenicity activity of green tea water extracts against environmental tobacco smoke. Furthermore, green tea has been reported as exhibiting cancer chemopreventive effects. (See Katiyar K. S., Agarwal R., Zaim M. T., and Mukhtar H., Protection Against N-nitrosodiethylamine and Benzo[alpha] pyrene-induced Forestomach and Lung Tumorigenesis in A/J Mice by Green Tea, *Carcinogenesis*, vol. 14, no. 5, pp. 849–855 (1993); Suganuma M., Okabe S., Kai Y., Sueoka N., Sueoka E., and Fujiki, H., Synergistic Effects of (−)-Epigallocatechin Gallate with (−)-Epicatechin, Sulindac, or Tamoxifen on Cancer-Preventive Activity in the Human Lung Cancer Cell Line PC-9, Cancer Research 59, 44–47, Jan. 1, 1999).

A cigarette filter containing a specific galenic formulation of a rosemary extract is reported as being effective in reducing the free radicals found in smoke. (See I. Emani, C. Rolando, M. Rojas, K. Alexandrov, H. Scherf, and H. Bartsch: A Rosemary Cigarette Filter May Reduce Tobacco-Linked Cancer, *Biosyntech Chemopreventive Filter—Coresta*, pp. 3–10, October 2000).

Myrisiticin, a volatile aroma constituent of parsley leaf oil, is reported as being a possible cancer chemopreventive agent. (See Zheng G., Kenney P. M., Zhang J., and Lam L.

K. T., Inhibition of Benzo[alpha]pyrene-induced Tumorigenesis by Myrisiticin, a Volatile Aroma Constituent of Parsley Leaf Oil, *Carcinogenesis*, Vol. 13, no. 10, pp. 1921–1923 (1992)).

It is therefore known to use natural ingredients for smoke detoxification in humans. There is, however, a need for improving smoke detoxifying activity, using natural ingredient compositions.

SUMMARY

One embodiment of the present invention provides a method for effecting smoke detoxification in a human by using a composition that is made of effective amounts of supercritical extract and hydroalcoholic extract of turmeric.

DETAILED DESCRIPTION

One embodiment of the present invention provides a composition for effecting smoke detoxification in humans. The composition may contain effective amounts of supercritical extract and hydroalcoholic extract of turmeric. The composition may also contain effective amounts of (A) supercritical and hydroalcoholic extracts of ginger, (B) supercritical extracts of rosemary, parsley seed, peppermint and clove, (C) hydroalcoholic extracts of rosemary, parsley leaf, peppermint, and clove, and (D) an aqueous extract of green tea. The composition may impart improved smoke detoxification properties, compared to known compositions, for example, because it contains a turmeric extract prepared in a supercritical/hydroalcoholic dual extraction process. Known compositions, on the other hand, merely contain a turmeric extract prepared with only one of a supercritical extraction process or a hydroalcoholic extraction process.

Another embodiment provides a method for effecting smoke detoxification in humans, including (orally) administering, for a therapeutically effective period of time, an effective amount of the composition to a human exposed (directly or indirectly) to toxins related to forms of smoke, for example, from tobacco or other sources of partially combusted hydrocarbons. As such, the composition may be administered for a period of time sufficient to effect smoke detoxification in the human.

The (herbal) composition (excluding inactive ingredients) may be orally administered in a daily dosage of at least about 350 mg, or about 375 to 2000 mg. If the composition includes inactive ingredients, then the active ingredients (e.g., herbal extracts) of the composition may include any conventional amount used in orally administered compositions. The composition may be administered on a daily basis, for example, for a period of at least four weeks. Oral administration may be accomplished by ingesting the composition, for example, with water. The orally administered composition may be in any conventional form including, for example, capsules (hard and/or soft), tablets, elixirs, powders, granules, suspensions in water or non-aqueous media, sachets, etc. The orally administered composition may also be in the form of one or more soft gel capsules.

The meaning of the term "smoke detoxification" includes a reduction in elevated levels of mutagens and fibrinogens in humans. The elevated levels of such substances may be caused by the direct or indirect exposure of a human to smoke, for example, from tobacco, hydrocarbon combustion, burnt meat, and the like.

The turmeric extract may be a "full spectrum" extract of the herb, such that the extract may contain curcumin, as well as oils and other constituents that provide improved smoke detoxification activities. As such, the turmeric extract may contain not only active curcuminoid fractions but also naturally present protein antioxidant factors and valuable essential oil components such as turmerone. Conventional turmeric extracts, however, are prepared by merely isolating through solvent extraction (using, for example, acetone or methylene chloride) one constituent, specifically one or more curcuminoids.

Then, the turmeric extract may contain a supercritical extract of the plant's lipophilic fractions and a hydroalcoholic extract of the plant's hydrophilic fractions. The use of supercritical extraction allows the lipophilic constituents to not be degraded in the extraction process by solvent, oxygen and/or heat stress, as occurs in conventional extraction. The lipophilic constituents may thus be used in their purest and most concentrated form. As such, the turmeric extract allows consumers an opportunity to experience the healing and detoxifying properties of turmeric in its most complete form.

The turmeric extract includes unique scavenging and modulating abilities, which may be especially synergistic in combination with green tea water extract. The green tea water extract itself exhibits a not insignificant protective activity with respect to known mutagens. Peppermint and clove extracts are also inhibitors of cigarette and other smoke mutagenicity. Rosemary and parsley leaf extracts enhance (phase two) detoxification activities and enhance the composition's efficacy. Ginger extract has activity against both benzopyrene and tryptophan pyrolysates, and enhances the composition's bioavailability.

The turmeric supercritical and post-supercritical hydroalcoholic extracts may be prepared as follows. A turmeric root, which may be cryogenically ground to preserve heat sensitive components, may be subjected to supercritical extraction to obtain (i) an oil extract (hereinafter "the supercritical turmeric extract") containing delicate lipophilic (e.g., oil-soluble/non-polar) components and (ii) an oil-free residue. Suitable supercritical extraction processes that may be used to obtain the supercritical turmeric extract, for example, are disclosed in E. Stahl, K. W. Quirin, D. Gerard: Dense Gases for Extraction and Refining, *Springer Verlag* 1988, incorporated herein by reference.

It has been found that about 25–33 kilograms of crude turmeric may produce 1 kilogram of oil extract. The oil-free residue may then be extracted in a water/alcohol (e.g., water/ethanol) mixture, composed of 60–80 parts alcohol and 40–20 parts water. Extraction of the oil-free residue in the water/alcohol mixture yields a broad spectrum of polar constituents, including aqueous soluble components and curcuminoids (e.g., a full range of curcuminoids). The water/alcohol liquid may then be evaporated off, leaving a powdered extract residue, referred hereinafter as "the (post-supercritical) hydroalcoholic turmeric extract." It has been found that about 6 kilograms of oil-free turmeric residue may produce about 1 kilogram of post-supercritical hydroalcoholic turmeric extract. The post-supercritical hydroalcoholic extract may be combined or blended with the supercritical turmeric extract at a weight ratio of about 3.0–6.0 parts post-supercritical hydroalcoholic extract to 1 part supercritical turmeric extract. The post-supercritical hydroalcoholic extract and the supercritical extract may also be combined at a weight ratio of about 5.3 parts post-supercritical hydroalcoholic extract per 1 part supercritical turmeric extract. The supercritical and post-supercritical hydroalcoholic turmeric extracts may be separately added to and blended with other extracts, as long as the resulting composition contains the appropriate weight ratios of the supercritical and post-supercritical hydroalcoholic turmeric extracts.

The supercritical and post-supercritical hydroalcoholic extracts of ginger may be prepared using the procedures for preparing the supercritical and post-supercritical hydroalcoholic extracts of turmeric. The supercritical and post-supercritical hydroalcoholic ginger extracts may be blended together and then added to other herbal extracts. The resulting composition may contain the post-supercritical hydroalcoholic ginger extract and the supercritical ginger extract, both of which may be combined at a weight ratio of about 4.4 parts of post-supercritical hydroalcoholic extract to 1 part of supercritical extract.

In addition, the supercritical extracts of clove, peppermint, parsley seed and rosemary may be prepared using the procedures for preparing the supercritical turmeric and ginger extracts. Each of the hydroalcoholic extracts of clove, peppermint, parsley leaf and rosemary may be prepared by extracting the plant portion in a water/alcohol (e.g., water/ethanol) mixture, composed of 60–80 parts alcohol and 40–20 parts water. The water/alcohol liquid may then be evaporated off, leaving a powdered extract residue. For each of the clove, peppermint, parsley and rosemary, the supercritical and hydroalcoholic extracts may be blended together and then added to other herbal extract, or the supercritical and hydroalcoholic extracts may be separately added to and blended with other herbal extracts used in the composition.

The composition may contain a range of weight ratio(s) of: (i) the hydroalcoholic rosemary extract to the supercritical rosemary extract from about 1.75:1 to about 2.25:1, or about 2:1; (ii) the hydroalcoholic parsley leaf extract to the supercritical parsley seed extract from about 1.75:1 to about 2.25:1, or about 2:1; (iii) the post-supercritical hydroalcoholic ginger extract to the supercritical ginger extract from about 4:1 to about 6:1, or about 4.4:1; (iv) the hydroalcoholic peppermint extract to the supercritical peppermint extract from about 1.75:1 to about 2.25:1, or about 2:1; and/or (v) the hydroalcoholic clove extract to the supercritical clove extract from about 1.75:1 to about 2.25:1, or about 2:1. As described above, the post-supercritical hydroalcoholic turmeric extract and the supercritical turmeric extract may be combined at a weight ratio of about 3–6 parts of post-supercritical hydroalcoholic extract to 1 part of supercritical extract, or about 5.3 parts of post-supercritical hydroalcoholic extract to 1 part of supercritical extract.

The green tea water extract may be prepared by (i) soaking dry green tea leaves in water for a period of about 10 to 60 minutes, for example, at a temperature of 80° C. or lower, (ii) filtering the soaked leaves to obtain an aqueous extract, and (iii) drying the extract to obtain a (dried) solid material. Such an extraction process is described, for example, in R. Zhou et al., *Toxicology Letters* 115 (2000) 23–32, incorporated herein by reference. Another suitable extraction process for obtaining green tea water extract is described, for example, in S. K Katiyar et al., *Carcinogenesis*, vol. 14, no. 5, pp. 849–855 (1993), incorporated herein by reference.

The composition may contain a weight ratio of (i) the extracts of turmeric, rosemary, parsley, ginger, peppermint and clove to (ii) the extract of green tea of about 1:1 to about 2:1, or about 1.5:1.

The composition may also contain effective amounts (e.g., certain amounts that causes the composition to exhibit smoke detoxification properties) of each of the above mentioned extracts. The composition, for example, may contain by weight: (i) from about 45% to 55%, or about 50%, of the post-supercritical hydroalcoholic and supercritical turmeric extracts, where the post-supercritical hydroalcoholic and supercritical turmeric extracts may be present at the appropriate weight ratio relative to one another (see above); (ii) from about 1.5% to 2.5%, or about 2.0%, of the supercritical and hydroalcoholic rosemary extracts; (iii) from about 1.5% to 2.5%, or about 2.0%, of the supercritical parsley seed extract and hydroalcoholic parsley leaf extract; (iv) from about 1.5% to 2.5%, or about 2.0%, of the post-supercritical hydroalcoholic and supercritical ginger extracts, where the post-supercritical hydroalcoholic and supercritical ginger extracts may be present at the appropriate weight ratio relative to one another (see above); (v) from about 1.5% to 2.5%, or about 2.0%, of the supercritical and hydroalcoholic peppermint extracts; (vi) from about 1.5% to 2.5%, or about 2.0%, of the supercritical and hydroalcoholic clove extracts; and (vii) from about 35% to 45%, or about 40%, of the aqueous extract of green tea.

In addition, the supercritical extract of turmeric may contain about 43% to 47%, or about 45%, of turmerones. The post-supercritical hydroalcoholic extract of turmeric may contain a minimum of about 11%, or about 11% to 15%, of curcuminoids. The supercritical extract of ginger may contain about 28% to 32% of pungent compounds and about 6% to 10% of zingiberene, or about 30% of pungent compounds and about 8% of zingiberene. The post-supercritical hydroalcoholic extract of ginger may contain about 1% to 5%, or about 3%, of pungent compounds. The green tea aqueous extract may contain about 43% to 47%, or about 45%, of polyphenols. The supercritical extract of clove may contain about 63% to 67%, or about. 65%, of eugenol. The supercritical extract of parsley seed may contain about 23% to 27%, or about 25%, of myristicin. The supercritical extract of peppermint may contain about 33% to 37%, or about 35%, of menthol. The supercritical extract of rosemary may contain about 21% to 25%, or about 23%, of phenolic antioxidants. The hydroalcoholic extract of rosemary may contain about 21% to 25%, or about 23%, of phenolic antioxidants.

The composition may also contain a pharmaceutically acceptable carrier such as, for example, one or more pharmaceutically suitable: inactive excipients, carriers, diluents, lubricants, adjuvants, and lubricants. For example, inactive excipients, carriers, diluents, lubricants, and adjuvants may include: cellulose, substituted cellulose, calcium carbonate, dicalcium phosphate, starches, lactose, modified food starches, dextrose, calcium sulfate, magnesium carbonate, magnesium stearate, stearic acid, glycerin, vegetable oils, polysorbates, lecithin, silicium dioxide, food glaze, talc, croscarmellose sodium, povidone, water and gelatin. The (active-ingredient) composition may contain additional inactive excipients, carriers, diluents, lubricants and adjuvants such as, for example, disclosed in the Handbook of Food Additives (CRC Press), incorporated herein by reference (in relevant parts only). The pharmaceutically acceptable carrier may contain, for example, any conventional amount used in an orally administered composition.

The table below is an exemplary composition (excluding inactive ingredients), where the composition may be administered orally, for example, by a human. The amounts recited in the Table represent daily dosages of the ingredients listed.

TABLE

ORALLY ADMINISTERED COMPOSITION
DAILY DOSAGE

| | Supercritical Extract | Post Supercritical Ethanolic Extract | Ethanolic Extract | Aqueous Extract | Plant Part |
|---|---|---|---|---|---|
| Turmeric | 30 mg (45% turmerones - 13.5 mg) | 160 mg (minimum of 11% curcuminoids - 17.6 mg) | N/A | N/A | rhizome |
| Green Tea | N/A | N/A | N/A | 150 mg (45% polyphenols - 67.5 mg) | leaf |
| Clove | 2.5 mg (65% eugenol - 1.6 mg) | N/A | 5 mg (10:1) | N/A | bud |
| Ginger | 1.4 mg (30% pungent compounds - 0.4 mg, 8% zingiberene - 0.1 mg) | 6.1 mg (3% pungent compounds - 0.18 mg) | N/A | N/A | rhizome |
| Parsley | 2.5 mg (from seed) (25% myristicin - 0.6 mg) | N/A | 5 mg (from leaf) (8:1) | N/A | seed/leaf |
| Peppermint | 2.5 mg (35% menthol - 0.85 g) | N/A | 5 mg (4:1) | N/A | leaf |
| Rosemary | 2.5 mg (23% total phenolic antioxidants - 0.58 mg) | N/A | 5 mg (23% total phenolic antioxidants - 1.15 mg) | N/A | leaf |

The composition presented in the Table above may also contain inactive ingredients such as, for example, olive oil (extra virgin), maltodextrin, and yellow beeswax. The capsule form of the composition may further contain gelatin, vegetable glycerin, purified water and carob. The composition presented in the Table above may be in the form of one soft gel capsule, where the amounts listed may constitute a single serving or unit dose of the composition. The capsule may be administered using 8 ounces of water or another liquid. Furthermore, two or more capsules of the composition may be taken daily, for example, if exposed to high(er) levels of smoke.

The foregoing presentation of the described embodiments is provided to enable any person skilled in the art to make or use the present invention. Various modifications to these embodiments are possible, and the generic principles presented herein may be applied to other embodiments as well. As such, the present invention is not intended to be limited to the embodiments shown above, and/or any particular configuration of structure or composition but rather is to be accorded the widest scope consistent with the principles and novel features disclosed in any fashion herein.

What is claimed is:

1. A method for effecting smoke detoxification in a human comprising administering a composition comprising effective amounts of a supercritical extract and hydroalcoholic extract of turmeric to said human.

2. The method of claim 1, wherein a weight ratio of the hydroalcoholic extract to the supercritical extract includes a weight ratio of about 3.0–6.0 parts hydroalcoholic extract to 1 part supercritical extract.

3. The method of claim 1, wherein the composition includes at least one of curcuminoids, antioxidants, and turmerone.

4. The method of claim 1, wherein the supercritical extract of turmeric contains about 43% to 47% of turmerones, and wherein the hydroalcoholic extract of turmeric contains about 11% to 15% of curcuminoids.

5. The method of claim 1, wherein the composition is further made of an effective amount of an aqueous extract of green tea, and wherein at least one of the supercritical extract and the hydroalcoholic extract of turmeric is synergistic in combination with the aqueous extract of green tea.

6. The method of claim 1, wherein the composition is orally administered, for a therapeutically effective period of time, to the human exposed to toxins from smoke.

7. The method of claim 6, wherein the composition is used to reduce elevated levels of mutagens and fibrinogens in the human exposed to toxins from smoke.

8. A method for effecting smoke detoxification in a human comprising administering a composition comprising effective amounts of (i) supercritical and hydroalcoholic extracts of turmeric and ginger, (ii) supercritical extracts of rosemary, parsley seed, peppermint and clove, and (iii) hydroalcoholic extracts of rosemary, parsley leaf, peppermint and clove to said human.

9. The method of claim 8, wherein a weight ratio of the hydroalcoholic turmeric extract to the supercritical turmeric extract includes a weight ratio of about 3.0–6.0 parts hydroalcoholic extract to 1 part supercritical extract.

10. The method of claim 8, wherein a weight ratio of the hydroalcoholic ginger extract to the supercritical ginger extract includes a weight ratio of about 4.4 parts of the hydroalcoholic extract to 1 part of the supercritical extract.

11. The method of claim 8, wherein the composition further comprises effective amounts of an aqueous extract of green tea.

12. The method of claim 11, wherein the composition contains weight ratios of: (i) the hydroalcoholic rosemary extract to the supercritical rosemary extract from about 1.75:1 to 2.25:1; (ii) the hydroalcoholic parsley leaf extract to the supercritical parsley seed extract from about 1.75:1 to 2.25:1: (iii) the hydroalcoholic ginger extract to the supercritical ginger extract from about 4:1 to 6:1; (iv) the hydroalcoholic peppermint extract to the supercritical peppermint extract from about 1.75:1 to 2.25:1; (v) the hydroalcoholic clove extract to the supercritical clove extract from about 1.75:1 to 2.25:1, and (vi) the extracts of turmeric, rosemary, parsley, ginger, peppermint and clove to the extract of green tea from about 1:1 to 2:1.

13. The method of claim 11, wherein the composition contains by weight: (i) from about 45% to 55% of the hydroalcoholic and supercritical turmeric extracts; (ii) from about 1.5% to 2.5% of the supercritical and hydroalcoholic rosemary extracts; (iii) from about 1.5% to 2.5% of the supercritical parsley seed extract and hydroalcoholic parsley leaf extract; (iv) from about 1.5% to 2.5% of the hydroalcoholic and supercritical ginger extracts; (v) from about 1.5% to 2.5% of the supercritical and hydroalcoholic peppermint extracts; (vi) from about 1.5% to 2.5% of the supercritical and hydroalcoholic clove extracts; and (vii) from about 35% to 45% of the aqueous extract of green tea.

\* \* \* \* \*